US006403646B1

(12) United States Patent
Perlmutter et al.

(10) Patent No.: US 6,403,646 B1
(45) Date of Patent: Jun. 11, 2002

(54) METHOD FOR THE TREATMENT OF ALPHA-1-ANTITRYPSIN DEFICIENCY AND RELATED PATHOLOGIES

(76) Inventors: David H. Perlmutter, Children's Hospital of Pittsburgh, 3705 Fifth Ave., Pittsburgh, PA (US) 15213; Jon A. J. Burrows, WU School of Medicine, 4905 Children's Pl., Room 5309, St. Louis, MO (US) 63110; Lauren K. Willis, Center for Pediatric Research, 855 W. Brambleton Ave., Norfolk, VA (US) 23510-1001; Jeffery H. Teckman, WU School of Medicine, 4905 Children's Pl., Room 5309, St. Louis, MO (US) 63110

(*) Notice: Subject to any disclaimer, the term of this patent is extended or adjusted under 35 U.S.C. 154(b) by 0 days.

(21) Appl. No.: 09/608,324

(22) Filed: Jun. 30, 2000

Related U.S. Application Data
(60) Provisional application No. 60/141,685, filed on Jun. 30, 1999.

(51) Int. Cl.[7] .............................................. A61K 31/192
(52) U.S. Cl. ........................ 514/570; 514/569; 514/568
(58) Field of Search ................................ 514/570, 569, 514/568

(56) References Cited

U.S. PATENT DOCUMENTS

| | | | |
|---|---|---|---|
| 5,093,316 A | 3/1992 | Lezdey et al. ................ 514/8 |
| 5,635,533 A | 6/1997 | Samid ........................ 514/538 |
| 5,654,333 A | 8/1997 | Samid ........................ 514/538 |
| 5,712,307 A | 1/1998 | Samid ........................ 514/538 |
| 5,852,056 A | 12/1998 | Samid ....................... 514/510 |

OTHER PUBLICATIONS

Anon., The Medical Letter, 38(988), pp. 105–106 (1996).*
Rueda et al., Ann. Internal Medicine, (Jun. 1, 1998) 128, pp. 956–957 (abstract).*
Lomas et al., The mechanism of Z $\alpha_{-1}$–antitrypsin accumulation in the liver, *Nature*, Jun. 1992, vol. 357, pp. 605–607.
Sidhar et al., Mutations Which Impede Loop/Sheet Polymerization Enhance the Secretion of Human $\alpha_{-1}$–Antitrypsin Deficiency Variants, *J. Biol. Chem.*, 1995, vol. 270, No. 15, pp. 8393–8396.
Carlson et al., Accumulation of PiZ $\alpha_{-1}$–Antitrypsin Causes Liver Damage in Transgenic Mice, *J. Clin. Invest.*, 1989. vol. 83, pp. 1183–1190.
Dycaico et al., Neonatal Hepatitis Induced by $\alpha_{-1}$–Antitrypsin: A Transgenic Mouse Model, *Science*, 1988, vol. 242, pp. 1409–1412.
Wu et al., A lag in intracellular degradation of mutant $\alpha_{-1}$–antitrypsin correlates with the liver disease in homozygous PiZZ $\alpha_{-1}$–antitrypsin deficiency, *Proc. Natl. Acad. Sci. USA*, 1994, vol. 91, pp. 9014–9018.

Perlmutter., Alpha–1–antitrypsin Deficiency: Biochemistry and Clinical Manifestations, *Ann. Med.*, 1996, vol. 28, pp. 385–394.
Brusilow, Phenylacetyglutamine May Replace Urea as a Vehicle for Waste Nitrogen Excretion, *Pediatr. Res.*, 1991, vol. 29, No. 2, pp. 147–150.
Newmark et al., Butyrate and Phenylacetate as Diffenentiating Agents: Practical Problems and Opportunities, *J. Cell. Biochem.*, 1995, vol. 22, pp. 247–253.
Kruh, Effects of Sodium butyrae, a new pharmacological agent, *Molec. Cell. Biochem.*, 1982, vol. 42, pp. 65–82.
Carducci et al., Phenylbutyrate Induces Apoptosis in Human Prostate Cancer and Is More Potent Than Phenylacetate, *Clin. Cancer Res.*, 1995, vol. 2, pp. 379–387.
Ram et al., Growth Inhibition, Tumor Maturation, and Extended Survival in Experimental Brain Tumors in Rats Treated with Phenylacetate, *Cancer Res.*, 1994, vol. 54, pp. 2923–2927.
Collins et al., Oral Sodium Phenylbutyrate Therapy in Homozygous β Thalassemia: A Clinical Trial, *Blood*, 1995, vol. 85, No. 1, pp. 43–49.
Perrine et al., Butyrate Derivatives New Agents of Stimulating Fetal Globin Production in the β–Globin Disorders, *Am. J. Ped. Hematology/Oncology*, 1994, vol. 16, No. 1, pp. 67–71.
Kemp, et al., Gene redundancy and pharmacological gene therapy: Implications for X–linked adrenoleukodystrophy, *Nature Medicine*, 1998, vol. 4, No. 11, pp. 1261–1268.
Rubenstein et al., A Pilot Clinical Trial of Oral Sodium 4–Phenylbutyrate (Buphenyl) in ΔF508–Homozygous Cystic Fibrosis Patients, *Am. J. Crit. Care Med.*, 1998, vol. 157, pp. 484–490.
Zeitlin, Novel pharmacologic therapies for cystic fibrosis, *J. Clin. Invest.*, 1999, vol. 103, No. 4, pp. 447–452.
Rubenstein et al., In Vitro Pharmacologic Restoration of CFTR–mediated Chloride Transport with Sodium 4–Phenylbutyrate in Cystic Fibrosis Epithelial Cells Containing ΔF508–CFRT, *J. Clin. Invest.*, 1997, vol. 100, No. 10, pp. 2457–2465.
Rubenstein et al., Sodium 4–phenylbutyrate downregulations Hsc70: implications for intracellular trafficking of ΔF508–CFTR, *Am. J. Physiol. cell. Physiol.*, 2000, vol. 278, pp. C259–C258–C267.

* cited by examiner

*Primary Examiner*—Phyllis G. Spivack
(74) *Attorney, Agent, or Firm*—Senniger, Powers, Leavitt & Roedel

(57) ABSTRACT

A method for the treatment of alpha-1-antitrypsin deficiency caused by the protease inhibitor type Z mutation by administration of phenylbutyric acid derivatives. Also disclosed are methods for the prevention and treatment of liver injury and emphysema associated with alpha-1-antitrypsin deficiency by administration of phenylbutyric acid derivatives.

49 Claims, 8 Drawing Sheets

| CHEMICAL CHAPERONE | % α1-ATZ DELIVERED TO EC FLUID |
|---|---|
| CONTROL | 3% ±1% |
| GLYCEROL [10%] | 25% ±4.5% |
| 4-PBA [10mM] | 17% ±3% |
| TMAO [150mM] | 3% ±1% |
| D$_2$O | 3% ±1% |
| BETAINE [75mM] | 3% ±1% |

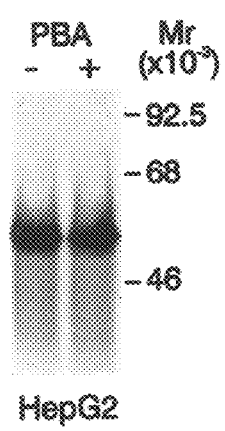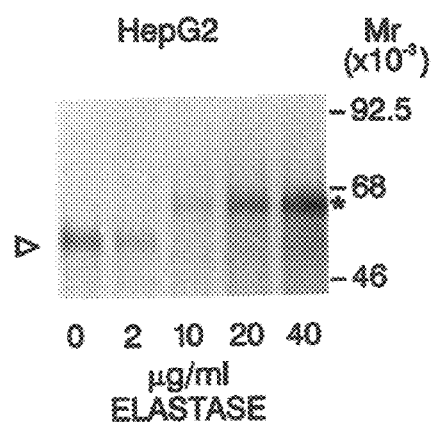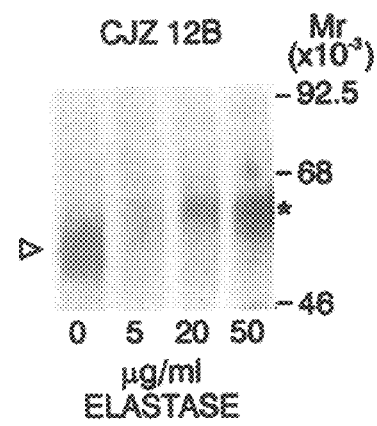

FIG. 6A  EFFECT OF TEMPERATURE ON α1-ATZ
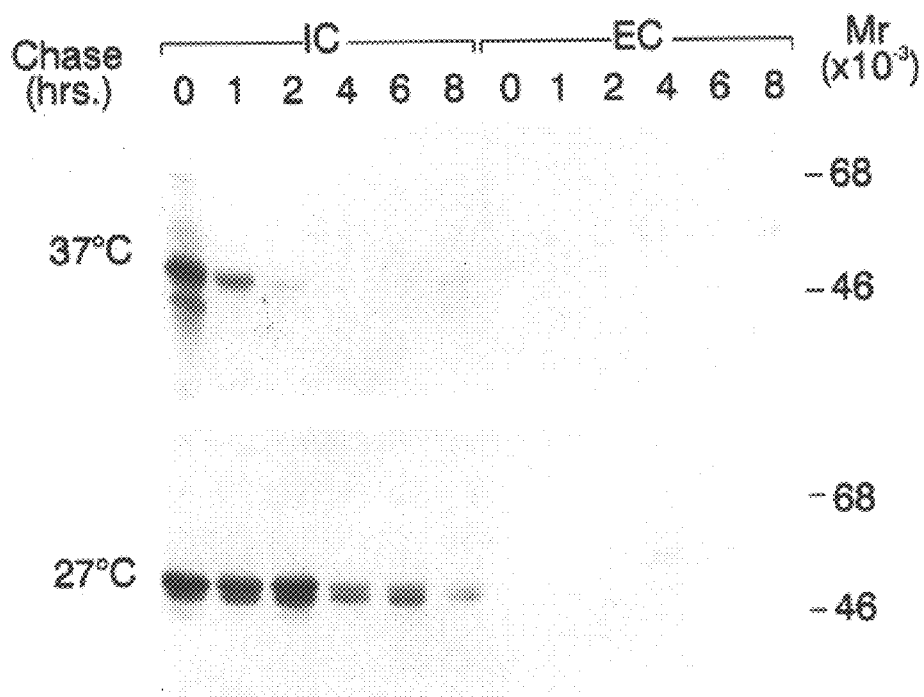
FIG. 6B
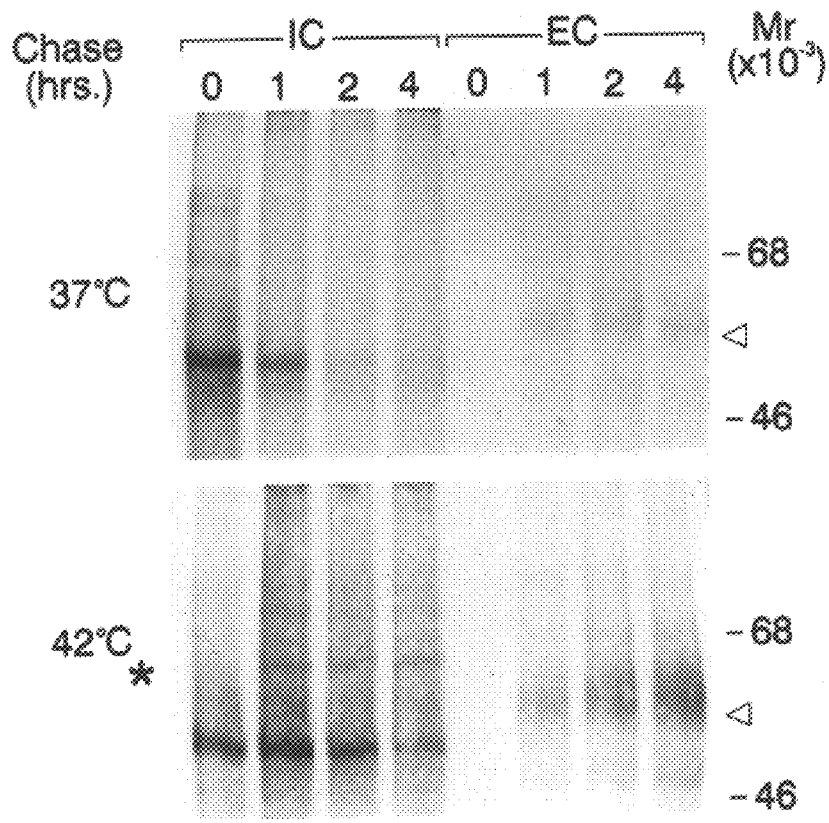

METHOD FOR THE TREATMENT OF ALPHA-1-ANTITRYPSIN DEFICIENCY AND RELATED PATHOLOGIES

CROSS-REFERENCE TO RELATED APPLICATIONS

This application claims priority to U.S. provisional application Ser. No. 60/141,685 filed Jun. 30, 1999 and herein incorporated by reference in its entirety for all purposes.

GOVERNMENT INTERESTS

This invention was made with government support under grants HL37784, DK52526, and HD07049 awarded by the National Institutes of Health. The Government has certain rights in this invention.

FIELD OF THE INVENTION

This invention relates to methods for the use of phenylbutyric acid and its pharmaceutically acceptable derivatives to treat alpha-1-antitrypsin deficiency in vertebrate animals. More particularly this invention relates to the treatment and prevention of pathologies resulting in alpha-1-antitrypsin deficiency including liver disease and emphysema. More particularly, this invention relates to the use to phenylbutyric acid and its pharmaceutically acceptable derivatives to increase secretion by the liver of alpha-1-antitrypsin in animals with alpha-1-antitrypsin deficiency caused by the protease inhibitor type Z (PiZ) mutation.

BACKGROUND

Alpha-1-antitrypsin deficiency is a relatively common genetic disorder that predisposes affected individuals to liver disease and/or pulmonary emphysema. The most common type of alpha-1-antitrypsin deficiency termed protease inhibitor type Z (PiZ), is transmitted as an autosomal recessive trait and affects approximately 1 in 1700 live births in most Northern European and North American populations. The PiZ mutation is a single nucleotide substitution that results in a single amino acid substitution (glutamate 342 to lysine). The replacement of glutamate 342 with a lysine apparently prevents normal folding of the protein. Although not all individuals with the PiZ mutation develop clinical symptoms, it is the most common genetic cause of acute and chronic liver disease in children and the most common genetic diagnosis in children undergoing liver transplantation. The incidence of emphysema or destructive lung injury in this population is not known, but cigarette smoking markedly increases the likelihood of lung injury and accelerates the course of the disease in PiZ individuals.

The major physiological function of alpha-1-antitrypsin is the inhibition of neutrophil elastase, cathepsin G and proteinase 3. The alpha-1-antitrypsin produced in individuals with PiZ alpha-1-antitrypsin deficiency is functionally active, although there may be a decrease in its specific elastase inhibitory capacity. The predominant site of alpha-1-antitrypsin synthesis is the liver, however, it is also synthesized in extrahepatic cell types including macrophages, intestinal epithelial cells and intestinal Paneth cells. In human hepatoma cells alpha-1-antitrypsin is synthesized as a 52 kD precursor that undergoes post translational dolichol phosphate-linked glycosylation at three asparagine residues, and also undergoes tyrosine sulfation. The protein is secreted as a 55 kD native single-chain glycoprotein with a half-time for secretion of 35 to 40 minutes. The half-life in plasma of type M alpha-1-antitrypsin ($\alpha$1-AT) (PiM is the normal allotype) is approximately five days. The half-life of the PiZ mutant protein ($\alpha$1-ATZ) is slightly less, but this difference is insufficient to account for the low plasma levels of alpha-1-antitrypsin in homozygous PiZ individuals.

Studies have provided evidence that the substitution of lysine for glutamate 342 in the PiZ mutant reduces the stability of the protein in monomeric form and increases the likelihood that it will form polymers by the so-called "loop-sheet" insertion mechanism. Lomas et al., *Nature*, 357:605–7, 1992. The presence of polymers of alpha-1-antitrypsin in the endoplasmic reticulum (ER) of individuals homozygous for the PiZ mutation suggest that polymerization may be responsible for the retention of $\alpha$1-ATZ in the ER. Further evidence that polymerization is responsible for retention of $\alpha$1-ATZ in the ER has been provided by studies in which the fate of $\alpha$1-ATZ was determined after introduction of additional mutations. For example, a mutation at amino acid 51, which is remote from the Z mutation and which impedes loop-sheet polymerization, was found to partially correct the intracellular retention of $\alpha$1-ATZ in microinjected Xenopus oocytes. Sidhar et al., *J. Biol. Chem.*, 270:8393–96, 1995.

Secretory glycoproteins ordinarily undergo a series of transient interactions with molecular chaperones in the ER until the folding or assembly process is complete. Once a translocation-competent conformation is achieved, secretory proteins dissociate from molecular chaperones to allow for subsequent transport. If a translocation-competent conformation is not achieved, as might occur with the abnormally folded PiZ alpha-1-antitrypsin molecule, the proteins do not dissociate from their chaperones and thus are retained in the ER until degraded. In individuals with PiZ alpha-1-antitrypsin deficiency, $\alpha$1-ATZ is translocated into the lumen of the ER where it associates with molecular chaperones. But, because of its amino acid substitution, the mutant $\alpha$1-ATZ protein is much less efficient at folding into a translocation-competent shape so that only about 15% of the newly synthesized molecules dissociate from their chaperones and proceed to the Golgi.

The major pathological finding of alpha-1-antitrypsin deficiency is periodic acid-Schiff-positive diastase-resistant globules in the ER of liver cells. As discussed previously, the retention of the PiZ mutant form of alpha-1-antitrypsin in the ER is due to the abnormal folding of the PiZ protein which results in a defect in transport of the protein from the ER to the Golgi. Evidence from studies using transgenic mice suggests that the liver injury seen in alpha-1-antitrypsin deficiency is directly due to the retention of the abnormally folded $\alpha$1-ATZ protein in the ER. Carlson et al., *J. Clin. Invest.*, 83:1183–90, 1988; Dycaico et al., *Science*, 242:1409–12, 1988. The reason that not all individuals with the PiZ mutation develop liver disease appears to be due to differences in the rate of degradation of $\alpha$1-ATZ within the ER. Studies have indicated that individuals that do not develop liver disease (protected individuals) degrade $\alpha$1-ATZ more rapidly that do individuals who develop liver disease (susceptible individuals). Wu et al., *Proc. Natl. Acad. Sci. USA*, 91:9014–18, 1994. Thus, conditions or treatments that either increase expression of the PiZ gene or decrease degradation of the mutant protein would be harmful, since they would only serve to increase the accumulation of mutant protein in the ER.

The pathogenesis of lung injury in alpha-1-antitrypsin deficiency is attributable to the marked reduction in available alpha-1-antitrypsin activity. Alpha-1-antitrypsin has been found to constitute greater than 90% of the neutrophil elastase inhibitor activity in pulmonary alveolar lavage fluid.

Thus, it appears that the destructive lung disease seen in many individuals with alpha-1-antitrypsin deficiency is due to a perturbation in the net balance between elastase and alpha-1-antitrypsin within the lungs. The uninhibited activity of neutrophil elastase, cathepsin G and proteinase 3, in turn, results in slow destruction of the connective tissue integrity of the lungs. This destruction of connective tissue leads to over distension and a reduction in the retractive force of the lungs which results in decreased expiratory airflow. Smoking exacerbates the problem by causing oxidative inactivation of what alpha-1-antitrypsin is present.

At present, treatment options for individuals with pathologies associated with alpha-1-antitrypsin deficiency are limited. Liver disease associated with alpha-1-antitrypsin deficiency is treated by orthotopic liver transplantation. Perlmutter, *Ann. Med.* 28:385–94, 1996. The limited supply of livers available for transplantation, the need to maintain transplant patients on anti-rejection drugs, and the cost involved in transplantation surgery, point out the need for alternative treatment methods. Patients with emphysema related to alpha-1-antitrypsin deficiency have been treated with purified plasma alpha-1-antitrypsin administered intravenously or by intratracheal aerosol administration. Lezdey et al., U.S. Pat. No. 5,093,316. The efficacy of this treatment regime, however, has yet to be established. Somatic gene therapy to replace the defective alpha-1-antitrypsin gene has been discussed, but has yet to be successfully used. One potential complication to replacement therapy with either purified alpha-1-antitrypsin protein or the alpha-1-antitrypsin gene is that the individuals treated have high levels of free elastase which, if the treatment is effective, would be expected to generate high levels of elastase-alpha-1-antitrypsin complexes. These complexes, through the serpin-enzyme complex (SEC) receptor, stimulate the synthesis of alpha-1-antitrypsin. In individuals with alpha-1-antitrypsin deficiency, this would lead to an increase in the amount of α1-ATZ protein retained in the ER predisposing the patient to liver injury. As used herein, the terms liver disease and liver injury include, but are not limited to, hepatic carcinomas.

What is needed, therefore, is a treatment for alpha-1-antitrypsin deficiency which stimulates secretion of the mutant alpha-1-antitrypsin protein by liver cells without increasing synthesis of the protein. Ideally, this treatment should be easy to administer and have few if any side effects, thus making it suitable for long-term administration.

It has been discovered that derivatives of butyric acid and especially phenyl butyric acid increase the secretion of α1-ATZ. For a number of years, phenylbutyric acid (PBA) has been used to treat urea cycle enzyme deficiencies where it functions as an ammonia scavenger. Brusilow, *Pediatr. Res.*, 29:147–50, 1991. Butyric acid derivatives, including PBA, have also been used to treat other conditions. Butyric acid derivatives have been shown to influence cell differentiation in a number of cell types and by a variety of mechanisms. Samid, U.S. Pat. No. 5,635,533; Newmark et al., *J. Cell. Biochem. Suppl.*, 22:247–53, 1995; Kruh, *Molec. Cell. Biochem.*, 42:65–82, 1982. Their effect on cell differentiation has led to the use of butyric acid derivatives as chemotherapeutic agents for cancer treatment and prevention. Samid, U.S. Pat. Nos. 5,852,056, 5,654,333; Carducci et al., *Clin. Cancer Res.*, 2:379–87, 1996; Ram et al., *Cancer Res.*, 54:2923–27, 1994. The ability of butyric acid derivatives to stimulate production of fetal hemoglobin has been used as a treatment for hemoglobin disorders. Samid, U.S. Pat. No. 5,712,307; Collins et al., *Blood*, 85:43–49, 1995; Perrine et al., *Am. J. Ped. Hematology/Oncology*, 16:67–71, 1994. Phenylbutyric acid has been used to treat X-linked adrenoleukodystrophy by stimulating production of an alternative peroxisomal membrane protein. Kemp, et al., *Nature Medicine*, 4:1261–68, 1998. Butyric acid derivatives have also been reported to be useful in increasing the presence of chloride transporters in patients with cystic fibrosis. The exact mechanism by which this is accomplished is unknown. Rubenstein et al., *J. Clin. Invest.*, 100:2457–65, 1997; Zeitlin, *J. Clin. Invest.*, 103:447–52, 1999. There is evidence that phenylbutyric acid stimulates production of the chloride transporter. Rubenstein et al., *J. Clin. Invest.*, 100:2457–65, 1997. It has also been postulated that phenylbutyric acid may also act to provide thermal stabilization to the mutant transporter, thus decreasing degradation within the ER and increasing transport to the cell surface. Zeitlin, *J. Clin. Invest.*, 103:447–52, 1999.

SUMMARY

Accordingly, the present invention provides a method for the treatment of alpha-1-antitrypsin deficiency, especially alpha-1-antitrypsin deficiency caused by the protease inhibitor type Z mutation (PiZ). Also provided is a method for the prevention, inhibition and/or treatment of liver disease caused by alpha-1-antitrypsin deficiency, especially alpha-1-antitrypsin deficiency caused by the PiZ mutation. Additionally, the invention provides for a method for the treatment, inhibition and/or prevention of emphysema in animals with alpha-1-antitrypsin deficiency, especially alpha-1-antitrypsin deficiency caused by the PiZ mutation.

One aspect of the invention is to provide a method for the treatment of alpha-1-antitrypsin deficiency in vertebrate animals by administration of an alpha-1-antitrypsin secretion stimulating amount of a compound of formula I:

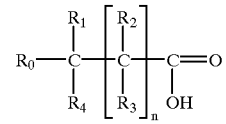

wherein $R_0$ is an aryl, phenoxy, substituted aryl or substituted phenoxy; $R_1$, $R_2$, $R_3$, and $R_4$ are independently, H, a lower alkoxy, a lower straight or branched chain alkyl or a halogen; and n is an integer from 0 to 2. The method includes pharmaceutically acceptable salts of formula I, mixtures of various compounds of formula I, and mixtures of pharmaceutically acceptable salts of various compounds of formula I.

Another aspect of the invention is to provide a method for the treatment of liver disease caused by alpha-1-antitrypsin deficiency by administering to a vertebrate animal with alpha-1-antitrypsin deficiency an alpha-1-antitrypsin secretion stimulating amount of a compound of formula I, where $R_1$, $R_2$, $R_3$, $R_4$, and n are as described above. Also included in this aspect are pharmaceutically acceptable salts of formula I, mixtures of formula I compounds, and mixtures of pharmaceutically acceptable salts of formula I compounds.

A further aspect of the invention is to provide a method for the prevention or inhibition of liver disease caused by alpha-1-antitrypsin deficiency by administering to a vertebrate animal with alpha-1-antitrypsin deficiency an alpha-1-antitrypsin secretion stimulating amount of a compound of formula I, where $R_1$, $R_2$, $R_3$, $R_4$, and n are as described above. Also included in this aspect are pharmaceutically acceptable salts of formula I, mixtures of formula I compounds, and mixtures of pharmaceutically acceptable salts of formula I compounds.

A further aspect of the invention is to provide a method for the treatment of emphysema in animals with alpha-1-antitrypsin deficiency by administering to a vertebrate animal with alpha-1-antitrypsin deficiency an alpha-1-antitrypsin secretion stimulating amount of a compound of formula I, where $R_1$, $R_2$, $R_3$, $R_4$, and n are as described above. Also included in this aspect are pharmaceutically acceptable salts of formula I, mixtures of formula I compounds, and mixtures of pharmaceutically acceptable salts of formula I compounds.

Yet another aspect of the invention is to provide a method for the prevention or inhibition of emphysema in animals with alpha-1-antitrypsin deficiency by administering to a vertebrate animal with alpha-1-antitrypsin deficiency an alpha-1-antitrypsin secretion stimulating amount of a compound of formula I, where $R_1$, $R_2$, $R_3$, $R_4$, and n are as described above. Also included in this aspect are pharmaceutically acceptable salts of formula I, mixtures of formula I compounds, and mixtures of pharmaceutically acceptable salts of formula I compounds.

Still another aspect of the invention is to provide a method for correcting alpha-1-antitrypsin deficiency by detecting the presence of alpha-1-antitrypsin deficiency in an animal, stimulating secretion of alpha-1-antitrypsin by administering an alpha-1-antitrypsin secretion stimulating amount of a compound of formula I, where $R_1$, $R_2$, $R_3$, $R_4$, and n are as described above, and monitoring the alpha-1-antitrypsin levels during and after treatment. Also included in this aspect are pharmaceutically acceptable salts of formula I, mixtures of formula I compounds, and mixtures of pharmaceutically acceptable salts of formula I compounds.

Yet another aspect provides a method for stimulating the secretion of alpha-1-antitrypsin by a cell comprising, contacting a cell containing a protease inhibitor type Z (PiZ) mutation with an alpha-1-antitrypsin secretion stimulating amount of a compound of formula I, where $R_1$, $R_2$, $R_3$, $R_4$, and n are as described above, and monitoring the alpha-1-antitrypsin levels during and after treatment. Also included in this aspect are salts of formula I, mixtures of formula I compounds, and mixtures of salts of formula I compounds.

BRIEF DESCRIPTION OF THE DRAWINGS

These and other features, aspects, and advantages of the present invention will become better understood with regard to the following description, appended claims, and accompanying drawings where:

FIG. 3(A) shows the effect of PBA on secretion of α1-ATZ in a murine hepatoma cell line. Molecular mass markers (in kDa) are shown at the right.

FIGS. 3(B) and 3(C) show the functional activity of α1-ATZ secreted by HepG2 (FIG. 3(B)) and CJZ12B (FIG. 3(C)) cells after treatment with 10 mM 4-phenylbutyric acid. Numbers along the bottom indicate the concentration (μg/ml) of purified human neutrophil elastase. The relative migration of the 55 kD native α1-ATZ in the extracellular fluid is indicated by the arrowhead on the left. The α1-ATZ-elastase complex is indicated by an asterisk at the right.

FIG. 6 shows the effect of temperature on the fate of α1-ATZ in CJZ12B cells. IC and EC indicate intracellular and extracelluar α1-ATZ, respectively. The relative migration of the 55 kD α1-ATZ protein in EC fluid is indicated by the arrowhead on the right.

ABBREVIATIONS

Figure 1A:
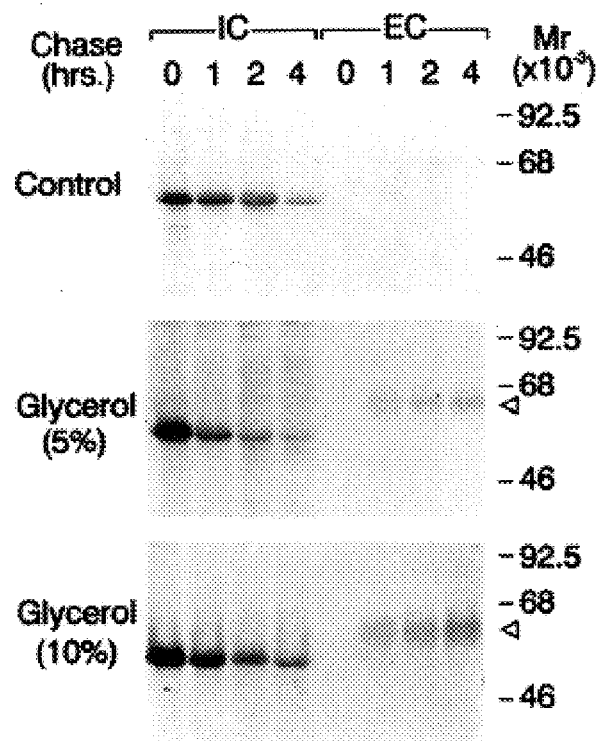
FIG. 1A shows the effect of treatment with 5% or 10% glycerol on synthesis, disappearance and secretion of α1-ATZ by CJZ12B cells. IC and EC indicate intracellular and extracellular α1-ATZ, respectively. Molecular mass markers (in kD) are shown at the right. The relative electrophoretic migration of 55 kD α1-ATZ is indicated on the right by a triangular arrowhead.
Figure 1B:
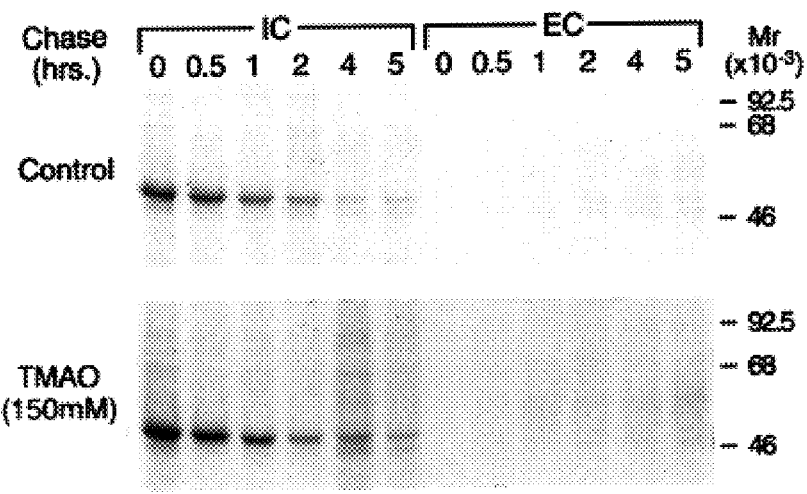
FIG. 1B shows the effect of treatment with 150 mM trimethylamine oxide (TMAO) on synthesis, disappearance and secretion of α1-ATZ by CJZ12B cells. IC and EC indicate intracellular and extracellular α1-ATZ, respectively. Molecular mass markers (in kD) are shown at the right. The relative electrophoretic migration of 55 kD α1-ATZ is indicated on the right by a triangular arrowhead.

PiZ=protease inhibitor type Z
α1-AT=type M alpha-1-antitrypsin (wild type)
α1-ATZ=type Z alpha-1-antitrypsin (mutant form)
SEC=serpin-enzyme complex
PBA=phenylbutryic acid
IC=intracellular
EC=extracellular
TMAO=trimethylamine oxide
PiZZ=homozygous type Z protease inhibitor phenotype
ER=endoplasmic reticulum

DETAILED DESCRIPTION

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

All publications, patents, patent applications and other references cited in this application are herein incorporated by reference in their entirety as if each individual publication, patent, patent application or other reference were specifically and individually indicated to be incorporated by reference.

As used herein, the terms carboxylic acid derivatives, phenylbutyric acid derivatives, PBA derivatives, phenylacetic acid derivatives, and PAA derivatives mean compounds of formula I:

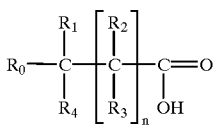

wherein

R$_0$ is an aryl, phenoxy, substituted aryl or substituted phenoxy. Suitable aryls include, without limitation, phenyl and napthyl. Substituted aryls and substituted phenoxys include, for example, and without limitation, one or more halogens (e.g. F, Cl, Br, I), lower alkyls (e.g. methyl, ethyl, propyl, butyl), or hydroxy substituents.

R$_1$, R$_2$, R$_3$, R$_4$ are independently an H, a lower alkoxy, a lower straight or branched chain alkyl, or a halogen. Lower alkoxy includes, but is not limited to, methoxy and ethoxy. Lower straight and branched chain alkyls include, but are not limited to, methyl, ethyl, propyl, and butyl. Halogens include, for example, F, Cl, Br, and I.

n is an integer from 0 to 2.

Also included are salts of formula I, for example, Na$^+$, K$^+$, or other pharmaceutically acceptable salts; stereoisomers of formula I; mixtures of compounds described by formula I; and mixtures of salts of compounds described by formula I.

When n is equal to two, each of the two R$_2$ and R$_3$ substituents may vary independently within the definition of formula I given above. It is intended that the definition of formula I include phenylbutyric acid, phenylbutyrate, phenylacetic acid and phenylacetate. As used herein, it is intended that mixtures include mixtures of compounds encompassed by formula I, for example, mixtures of phenylbutyric acid and phenylacetic acid; mixtures of salts of formula I compounds, for example, sodium phenylbutyrate and potassium phenylbutyrate, or sodium phenylbutyrate and sodium phenylacetate; and mixtures of an acid and a salt, for example, phenylbutyric acid and sodium phenylbutyrate. As used herein, references to a carboxylate such as phenylbutyrate or phenylacetate are intended to also refer to an appropriate counter ion, such as Na$^+$, K$^+$, or other pharmaceutically acceptable cation, including organic cations such as arginine. Some of the compounds defined by formula I can be interconverted when present in biological systems. For example, phenylbutyrate can be converted to phenylacetate and vice versa. As used herein, compounds of formula I include any compound formed as a result of a biochemical reaction within the host animal including any intermediaries formed.

Thus, the compounds intended to be included in the definition of formula I, include, but are not limited to, phenylbutyric acid, phenylproprionic acid, phenylacetic acid, phenylbutyrate, phenylproprionate, phenylacetate, phenoxybutyric acid, phenoxyproprionic acid, phenoxyacetic acid, phenoxybutyrate, phenoxyproprionate, phenoxyacetate, bromophenylbutyric acid, bromophenylproprionic acid, bromophenylacetic acid, bromophenylbutyrate, bromophenylproprionate, bromophenylacetate, chlorophenylbutyric acid, chlorophenylproprionic acid, chlorophenylacetic acid, chlorophenylbutyrate, chlorophenylproprionate, chlorophenylacetate, fluorophenylbutyric acid, fluorophenylproprionic acid, fluorophenylacetic acid, fluorophenylbutyrate, fluorophenylproprionate, fluorophenylacetate, iodophenylbutyric acid, iodophenylproprionic acid, iodophenylacetic acid, iodophenylbutyrate, iodophenylproprionate, iodophenylacetate, hydroxyphenylbutyric acid, hydroxyphenylproprionic acid, hydroxyphenylacetic acid, hydroxyphenylbutyrate, hydroxyphenylproprionate, hydroxyphenylacetate, methylphenylbutyric acid, methylphenylproprionic acid, methylphenylacetic acid, methylphenylbutyrate, methylphenylproprionate, methylphenylacetate, ethylphenylbutyric acid, ethylphenylproprionic acid, ethylphenylacetic acid, ethylphenylbutyrate, ethylphenylproprionate, ethylphenylacetate, naphthylbutyric acid, naphthylproprionic acid, naphthylacetic acid, naphthylbutyrate, naphthylproprionate, naphthylacetate. In particular it is intended that formula I include phenylbutyric acid, phenylbutyrate, phenylacetic acid, and phenylacetate. More particularly, it is intended to include 4-phenylbutyrate and 2-phenylacetate.

The compounds of the present invention can be formulated as pharmaceutical compositions. Such compositions can be administered orally, parenterally, by inhalation spray, rectally, vaginally, intradermally, transdermally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Hoover, John E., *Remington's Pharmaceutical Sciences*, Mack Publishing Co., Easton, Penn. (1975), and Liberman, H. A. and Lachman, L., Eds., *Pharmaceutical Dosage Forms*, Marcel Decker, New York, N.Y. (1980).

Injectable preparations, for example, sterile injectable aqueous or oleaginous suspensions, can be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and nonionic detergents, and polyethylene glycols can be used. Mixtures of solvents and wetting agents such as those discussed above are also useful.

Suppositories for rectal administration of the compounds discussed herein can be prepared by mixing the active agent with a suitable non-irritating excipient such as cocoa butter, synthetic mono-, di-, or triglycerides, fatty acids, or polyethylene glycols which are solid at ordinary temperatures but liquid at the rectal temperature, and which will therefore melt in the rectum and release the drug.

Solid dosage forms for oral administration may include capsules, tablets, pills, powders, and granules. In such solid dosage forms, the compounds of this invention are ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, or magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. The compounds can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of active ingredient that can be combined with the carrier materials to produce a single dosage form will vary depending upon the patient and the particular mode of administration.

The dosage required will vary according to a number of factors known to those skilled in the art, including, but not limited to, the compound or compounds used, the species of animal, the size of the animal, and the severity of the disease condition. For example, and without being bound by theory, a lower dosage may be suitable for prevention or inhibition of liver disease or emphysema associated with alpha-1-antitrypsin deficiency than is required for treatment of the conditions once clinical symptoms develop. In one embodiment, the dosage ranges from about 10 mg/kg body weight/day to about 1000 mg/kg body weight/day. In a another embodiment, the dosage is between about 250 mg/kg body weight/day to about 750 mg/kg body weight/day. In still another embodiment, the dosage is about 560 mg/kg body weight/day.

The compounds can be administered in a single dose, in multiple doses throughout a 24-hour period, or by continuous infusion. When administered by continuous infusion, the compounds can be supplied by methods well known in the art, such as, but not limited to, intravenous gravity drip, intravenous infusion pump, or implantable infusion pump. In one embodiment the total daily dose of the compounds is divided into four equal doses to be administered over a 24-hour period. Length of treatment will vary depending on many factors, for example, the severity of the condition and changes in clincal symptoms of conditions related to the alpha-1-antitrypsin deficiency. For example, treatment of the patient with the compounds of the invention may last until clinical symptoms of the related condition disappear, or more preferably, treatment will continue for the life of the patient.

As used herein, the terms "animal" and "vertebrate animal" include, but are not limited to, mammals, including human beings. It should be noted that the methods disclosed herein are applicable in both human and veterinary medicine. Thus, the methods can be applied to humans, domestic pets such as cats, dogs, rodents, birds etc., farm animals such as cows, sheep, goats, pigs, horses, etc., zoo animals, etc.

It has been discovered that administration of phenylbutyric acid (PBA) derivatives is effective in increasing the secretion of alpha-1-antitrypsin from cells containing a protease inhibitor type Z mutation and in particular cells homozygous for the Z mutation of the alpha-1-antitrypsin gene (PiZZ). PBA derivatives were found to be effective in stimulating secretion of Z type alpha-1-antitrypsin ($\alpha$1-ATZ), but not wild-type alpha-1-antitrypsin ($\alpha$1-AT) in a variety of cell types in vitro and in vivo. When used in vitro, PBA deriviatives can be effective at concentrations ranging from 0.1 mM to 100 mM. In one preferred embodiment, the in vitro concentration of PBA or a PBA derivative used is 10 mM. More importantly, PBA derivatives have been shown to increase levels of human $\alpha$1-ATZ by approximately 200 $\mu$g/ml in transgenic mice carrying the human PiZ alpha-1-antitrypsin gene. PBA derivatives apparently increase secretion of alpha-1-antitrypsin without increasing its de novo synthesis or increasing its degradation within the endoplasmic reticulum. The finding that PBA derivatives do not increase de novo synthesis is especially important, because intracellular accumulation of $\alpha$1-ATZ is thought to be the cause of liver damage associated with alpha-1-antitrypsin deficiency. Significantly, the PBA derivative 4-phenylbutyrate has been used for the long-term treatment of urea cycle disorders in humans without serious side effects. Thus, PBA derivatives are especially suitable for treatment of alpha-1-antitrypsin deficiency where long-term administration is required.

Because the pathologies associated with alpha-1-antitrypsin deficiency are due to low circulating levels of alpha-1-antitrypsin, administration of effective doses of PBA derivatives can be use to treat alpha-1-antitrypsin deficiency associated liver disease and emphysema. More importantly, administration of effective amounts of PBA derivatives to patients with alpha-1-antitrypsin deficiency can be used as a prophylactic means to prevent development of liver disease and emphysema or inhibit their progression. As used herein, "prevent" means to prevent the development of clinical symptoms. As used herein, "inhibit" means to stop the progression of the disease or to cause the disease to progress at a rate slower than would normally be expected.

The method of the present invention is not limited to administration of the compounds of formula I and their pharmaceutically acceptable salts, but also includes a process for treatment of alpha-1-antitrypsin deficiency and related pathologies comprising diagnosis of the alpha-1-antitrypsin deficiency, treatment with the compounds of the present invention, and monitoring of alpha-1-antitrypsin levels during and after the course of treatment.

Testing for alpha-1-antitrypsin deficiency can be carried out in the context of routine screening or to determine if alpha-1-antitrypsin deficiency is the underlying or contributing cause of an associated pathology such as liver disease or emphysema. Diagnosis of alpha-1-antitrypsin deficiency can be accomplished by a number of well-established techniques available through commercial clinical laboratories and which have been reviewed by Eriksson et al., *Baillieres Clin. Gastroenterol.*, 12:257–73, 1998. For example, serum or plasma levels of α1-AT can be measured by nephelometry or by immunoelectrophoresis. Phenotypic identification of α1-AT variants can be accomplished by a number of methods including isoelectric focusing (IEF) (Jeppsson et al., *Proc. Natl. Acad. Sci. USA*, 81:5690–93, 1994), or by DNA analysis (Kidd et al., *Nature*, 304:230–34, 1983; Braun et al., *Eur. J. Clin. Chem. Clin. Biochem.*, 34:761–64, 1996).

Following diagnosis, treatment can be accomplished by administration of the compounds of the present invention as previously described. As discussed previously, treatment can extend for a period to alleviate the clinical symptoms of the alpha-1-antitrypsin deficiency or more preferably, will continue throughout the life of the patient. It is preferred that alpha-1-antitrypsin levels in bodily fluids, preferably circulating blood levels, be monitored during and after treatment. Monitoring, however, is not required and can also be conducted only during treatment or only after treatment. Levels of α1-AT can be monitored by any of the techniques discussed previously for diagnosis of alpha-1-antitrypsin deficiency, including, but not limited to, nephelometry, immunoelectrophoresis, isoelectric focusing, or immunoassay. The exact monitoring schedule will vary with a number of factors, for example, the severity of the patient's condition, changes in the patient's health, availability of the patient for testing, cost, etc. Routine monitoring is preferably carried out at regular intervals, for example, every 6, 12, 18 or 24 months.

Although the examples hereinafter provided contain many specifics, these should not be construed as limiting the scope of the invention, but as merely providing illustrations of some of the aspects of the present invention.

EXAMPLES

Example 1

Several compounds were tested for their ability to stimulate secretion of the type Z alpha-1-antitrypsin protein in CJZ12B cells engineered for stable expression of type Z alpha-1-antitrypsin protein. Development of the cell line (CJZ12B) has previously been described. Wu et al., *Proc. Natl. Acad. Sci. USA*, 91:9014–18, 1994. The CJZ12B cell line is a fibroblast cell line derived from an individual homozygous for the Z mutation, but without liver disease. Cells were transduced with amphotropic recombinant retroviral particles using the method of Miller and Buttimore, *Mol. Cell. Biol.*, 6:2895–902, 1986. $pN_2$ Keller et al., *Nature*, 318:149–154, 1985) was used as the vector and the Rous sarcoma virus long terminal repeat was used as the promoter.

Example 2

CJZ12B cells were pre-incubated for 12 hours at 37° C. in serum-free Dulbecco's modified Eagle's medium (DMEM) control medium or serum-free DMEM medium supplemented with 10 mM 4-phenylbutyric acid (4-PBA or PBA), 5% glycerol, 10% glycerol, 150 mM trimethylamine oxide (TMAO), deuterated water ($D_2O$), or 75 mM betaine. Following pre-incubation, cells were subjected to pulse chase radiolabeling as described in Qu et al., *J. Biol. Chem.* 271:22791–95, 1996. Briefly, cells where incubated for an additional 2 hours at 37° C. in serum-free and methionine-free DMEM containing 250 μCi/ml of $^{35}S$-methionine. The cells were then rinsed rigorously and incubated in medium containing excess unlabeled methionine for intervals up to 10 hours as a chase period. At the end of the chase period, the extracellular medium was harvested and the cells lysed in phosphate-buffered saline (PBS), 1% Triton X-100, 0.5% deoxycholic acid, 10 mM EDTA, 2 mM phenylmethylsulfonyl fluoride. The radiolabeled cell lysates were subjected to clarification, immunoprecipitation, and the immunoprecipitates analyzed by SDS-PAGE/fluorography and densitometry using known methods. Wu et al., *Proc. Natl. Acad. Sci. USA*, 91:9014–18, 1994; Teckman & Perlmutter, *J. Biol. Chem.* 271:13215–20, 1996. Aliquots of the radiolabeled cell lysates were also subjected to trichloroacetic acid (TCA) precipitation and scintillation counting of the TCA precipitates to ensure that there was equivalent incorporation.

Figures 1C, 1D:
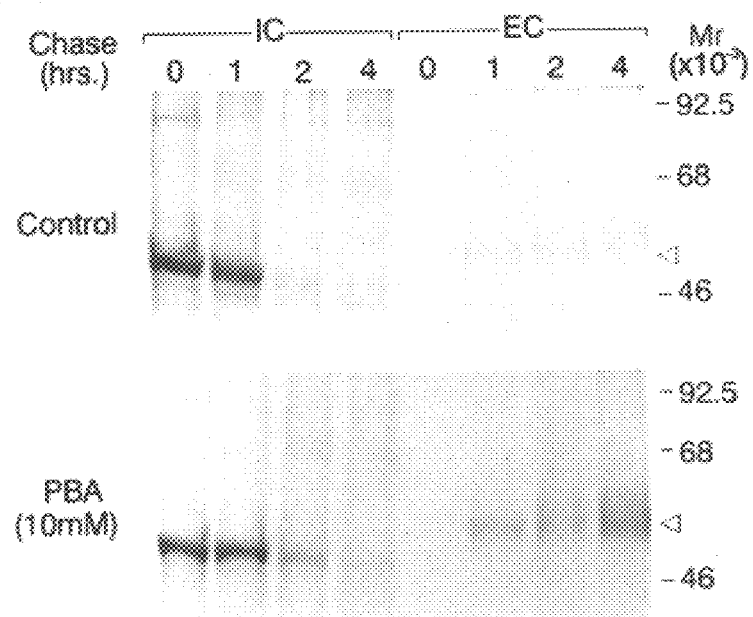
FIG. 1C shows the effect of treatment with 10 mM 4-phenylbutyric acid (PBA) on synthesis, disappearance and secretion of α1-ATZ by CJZ12B cells. IC and EC indicate intracellular and extracellular α1-ATZ, respectively. Molecular mass markers (in kD) are shown at the right. The relative electrophoretic migration of 55 kD α1-ATZ is indicated on the right by a triangular arrowhead.
FIG. 1D shows a summary of the results of treatment of CJZ12B cells with the chemical chaperones 10% glycerol, 10 mM 4-PBA, 150 mM TMAO, $D_2O$ or 75 mM betaine. Data are expressed as percent α1-ATZ delivered to the extracellular (EC) fluid after a 4 hour chase, compared with the total α1-ATZ newly synthesized at time 0, as determined by phosphoimaging and densitometric analysis of gels. Only experiments in which there was a similar amount of α1-ATZ at time 0 in control and experimental conditions were used. Values represent the mean ±1.0 standard deviation for percent α1-ATZ delivered to the extracellular fluid from at least three independent experiments.

The results showed that in the control group, α1-ATZ was synthesized as a 52 kD polypeptide that was retained for 2 hours and the progressively disappeared between 2 and 4 hours of the chase period. Only trace amounts of the 55 kD mature form of the protein were detected in the extracellular fluid (EC). In cells treated with 5% glycerol, α1-ATZ was also synthesized as a 52 kD polypeptide, but disappeared more rapidly, beginning between 1 and 2 hours into the chase period, and a substantial amount of the mature 55 kD form of the protein was secreted into the EC. FIG. 1A. When 10% glycerol was used the results were similar except that the amount of the 55 kD form of α1-ATZ secreted into the EC was even greater. Likewise, treatment with 4-phenylbutyric acid resulted in a marked increase in secretion of the mature 55 kD form of α1-ATZ into the EC. FIG. 1C. In contrast, TMAO (FIG. 1C), deuterated water and betaine had no significant effect. Table 1 shows the percent α1-ATZ secreted into the EC after a four hour chase, compared with the total α1-ATZ newly synthesize at time 0 after labeling. Only experiments where there were similar amounts of α1-ATZ present at time 0 were used.

The effect of glycerol and 4-PBA was specific for secretion of the mutant α1-ATZ protein. Neither compound altered the secretion of the endogenous complement protein factor H or total TCA-precipitable protein in the CJZ12B cells. In addition, 4-PBA did not alter the rate of disappearance of α1-ATZ from the intracellular compartment, suggesting that its effect predominantly involves an increase in translocation of the α1-ATZ molecules from the ER into the rest of the secretory pathway rather than an increase in ER degradation (FIG. 1C).

Example 3

Figure 2A:
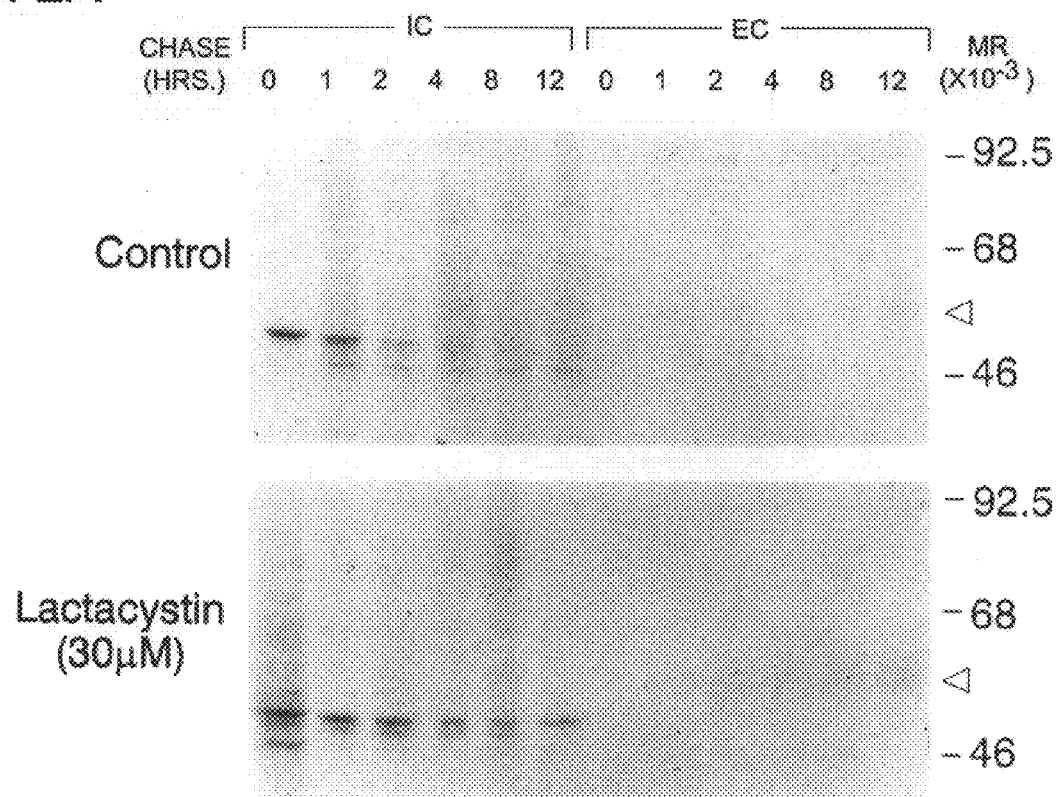
FIG. 2 shows the effect of lactacystin and cylcoheximide on the synthesis, disappearance and secretion of α1-ATZ by CJZ12B cells. IC and EC indicate intracellular and extracellular α1-ATZ, respectively. The relative migration of molecular mass markers are indicated by tick marks on the right and the expected relative migration of 55 kD α1-ATZ in extracelluar fluid is indicated by the arrowhead.
Figure 2B:
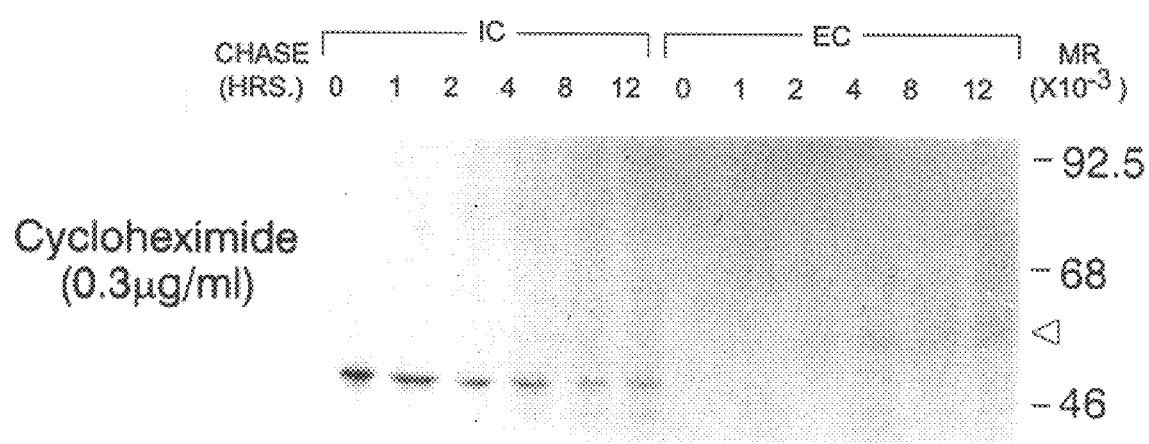

To determine whether decreased ER degradation results in increased secretion of α1-ATZ, two inhibitors of ER degradation of α1-ATZ, lactacystin and cycloheximide, were tested. Pulse-chase studies were conducted as described in Example 2. Treatment groups were control, 30 μM lactacystin, and 0.3 mg/ml cycloheximide. In the lactacystin group, cells were pre-incubated for two hours with lactacystin. In each case, the pulse period was one hour. Results were obtained and analyzed as in Example 2. The results are shown in FIG. 2. Both lactacystin and cycloheximide caused a decrease in the rate of disappearance of intracellular α1-ATZ, but there was no appearance of α1-ATZ in the EC fluid even after a 12 hour chase period. These results showed that increased secretion of α1-ATZ could not be achieved by inhibition of intra cellular degradation.

Example 4

In order to determine if the results obtained were not limited to fibroblast, but also applied to hepatoma cells, the effect on PBA on secretion of α1-ATZ was examined in a mouse heptoma cell line engineered for stable expression of the human α1-ATZ gene (Hepa 1-6N2Z4). Engineered cells were produced as described in Example 1. Experimental conditions were the same as those described in Example 2. The results are given in FIG. 3 and show that in the absence of PEA (control), there is a 52-kDa α1-ATZ polypeptide at t=0 in cell lysates (IC). This polypeptide was retained for 1 hour and then progressively disappeared between t=2 and 3 hours of the chase period with very little of the mature 55-kDa α1-ATZ polypeptide secreted into the EC medium. In the presence of PBA, a similar amount of the 52-kDa α1-ATZ was present in cell lysates at t=0. There was no significant difference in the kinetics of its disappearance from cell lysates during the chase period, but a substantial amount of the 55-kDa mature α1-ATZ appeared in the extracellular (EC) culture medium. These data show that α1-ATZ has a similar fate in murine hepatoma cells as in human fibroblast cell lines and the PBA mediates an increase in secretion of α1-ATZ in both cell types.

Example 5

Figure 4:
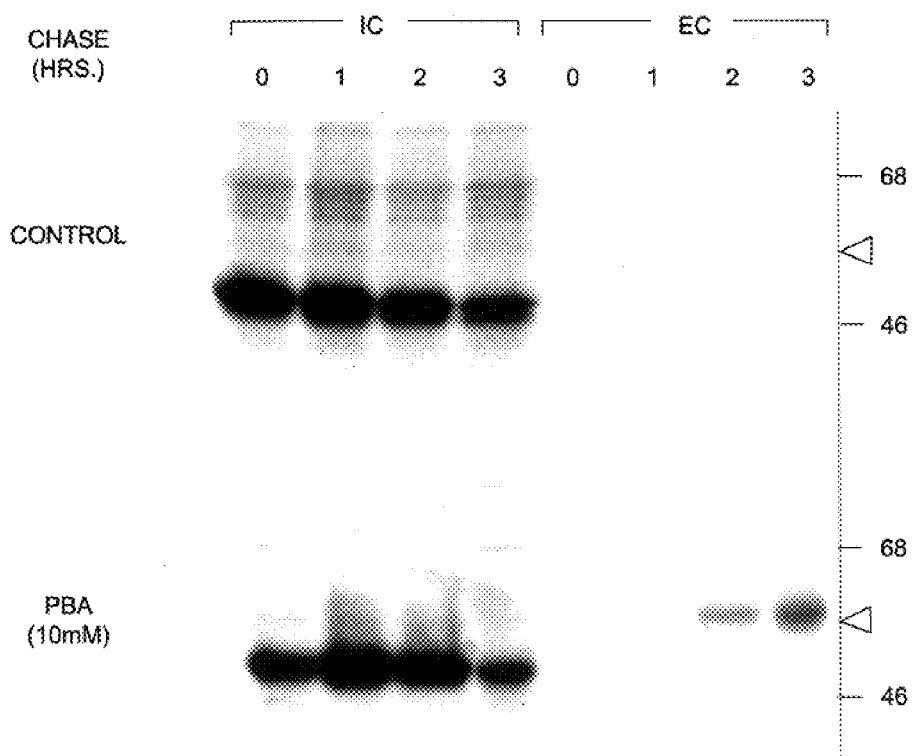
FIG. 4 shows the effect of 10 mM 4-phenylbutyric acid (PBA) on the synthesis of endogenous wild type α1-AT by the human hepatoma cell line HepG2.

Because the liver disease associated with alpha-1-antitrypsin deficiency is apparently caused by retention of α1-ATZ protein in the hepatic cells, it is important than any treatment not stimulate α1-ATZ synthesis. Therefore, the effect of 4-PBA on synthesis of α1-ATZ by the human hepatoma cell line HepG2 (ATCC # HB-8065; Knowles et al., *Science*, 209:497–99, 1980) was examined. The expression and regulation of wild-type α1-AT in HepG2 cells is similar to that seen in liver cells in vivo. Perlmutter et al., *J. Clin. Invest.* 84:1555–61, 1989. HepG2 cells were preincubated for 12 hours at 37° C. in serum-free DMEM with (treatment) or without (control) 10 mM 4-PBA. The cells were then pulse labeled for 20 minutes as described in Example 2. The cells were next lysed and the cell lysates analyzed by immunoprecipitation followed by SDS-PAGE/fluorography as described in Example 2. The results are shown in FIG. 4A. Addition of 10 mM 4-PBA, which causes increased secretion of α1-ATZ, had no effect on synthesis of wild-type α1-AT. These results show that butyric acid derivatives can increase secretion of alpha-1-antitrypsin without a concurrent increase in its synthesis.

Example 6

For the butyric acid derivatives to be effective as a treatment for alpha-1-antitrypsin deficiency, the α1-ATZ must be functional. HepG2 and CJZ12B cells were treated with 10 mM 4-PBA and subjected to pulse-chase labeling as described in Example 2. Aliquots of the EC fluid were incubated for 30 minutes at 37° C. with 0, 5, 20 and 40 μg/ml of purified human neutrophil elastase. The reaction was terminated by addition of phenylmethylsulfonyl fluoride (PMSF) to a concentration of 2 mM and the reaction mixtures subjected to immunoprecipitation and SDS-PAGE/fluorography as described in Example 2. The results are shown in FIG. 4B. The results show that most of the 55 kD α1-ATZ secreted in each case was progressively converted to a high molecular weight α1-ATZ-elastase complex with increasing concentrations of neutrophil elastase. These results are similar to those observed when purified human plasma α1-AT or α1-AT secreted by Caco2 cells is reacted with neutrophil elastase. Perlmutter et al., *J. Biol. Chem.*, 264:9485–90, 1989. Thus, the results indicate that the α1-ATZ secreted in response 4-PBA treatment is functionally active.

Example 7

Figure 5A:
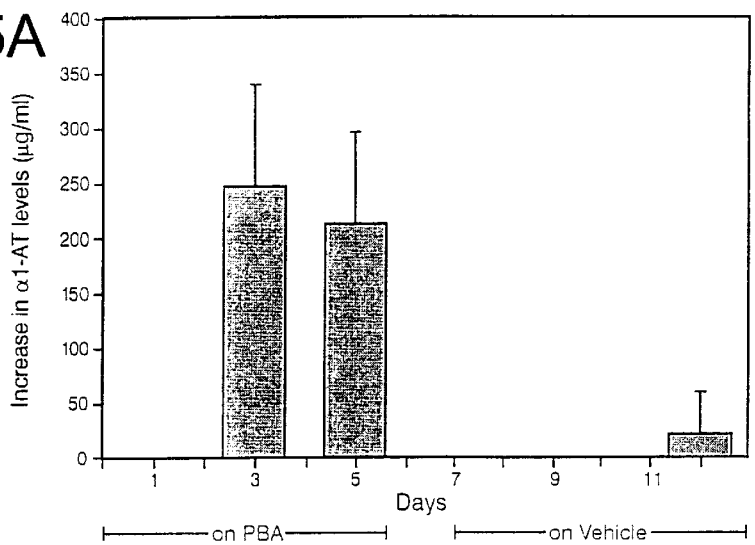
FIG. 5A shows the effect of treatment with 4-phenylbutyric acid on serum levels of human α1-ATZ in all seven transgenic mice. The graph shows the combined results for PBA in two trial periods at days 3 and 5 (while receiving PBA) and day 12 (off PBA for 7 days). Increases in α1-ATZ are in μg/ml compared with baseline (day 0). Error bars represent ±1.0 standard deviation. Days indicate day of the experiment.
Figure 5B:
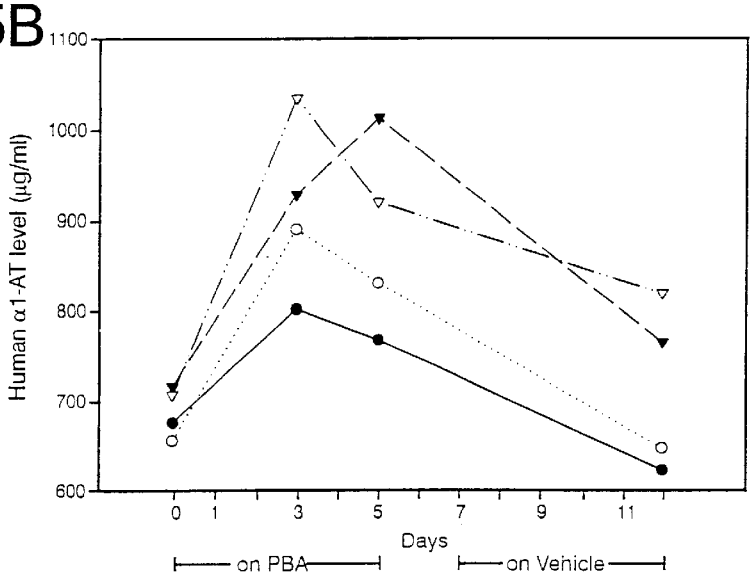
FIG. 5B shows the absolute leveles of human α1-ATZ in four mice with baseline levels of 600–700 μg/ml.
Figure 5C:
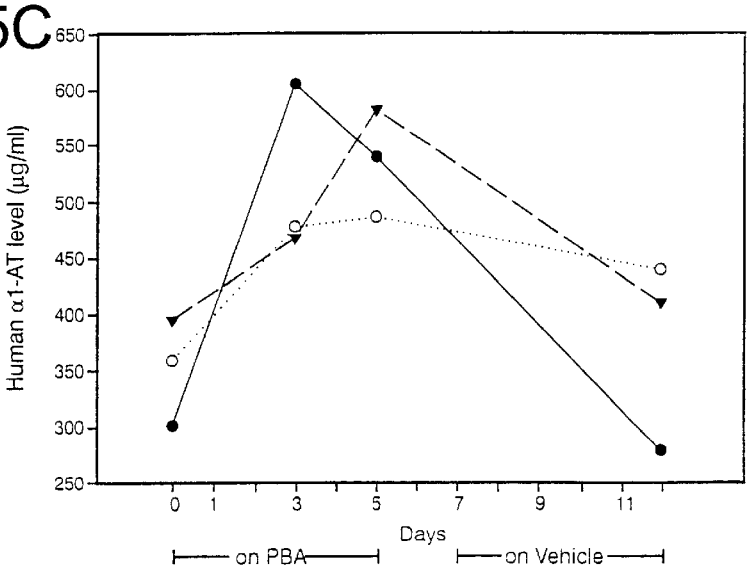
FIG. 5C shows the absolute levels of human α1-ATZ in three PiZ mice with lower baseline levels (300–400 μg/ml).

To determine whether butyric acid derivatives increase secretion of α1-ATZ in vivo, 4-PBA was administered to transgenic mice homozygous for the human α1-ATZ gene. PIZZ11.03 mice; Carlson et al., *J. Clin. Invest.*, 83:1183–90, 1989. Six to seven week old PIZZ11.03 mice were gavage fed, in three divided doses, either water (vehicle) or a total of 560 mg/kg body weight/day of 4-PBA for five days in a cross-over design. Blood was drawn from the tail vein prior to the initial day of treatment and on days 3, 5, 8, 12, 17, 19 and 22. Serum obtained was subjected to an ELISA for human α1-AT. Methods for conducting ELISA assays are well known to those skilled in the art. See, for example, Bullock et al., *ELISA Techniques: New Developments and Practical Applications in a Broad Field*, Academic Press, 1991; Kemeny et al., *ELISA and Other Solid Phase Immunoassays*, Chichester, 1988. Briefly, goat anti-human α1-AT IgG (Cappel) was used as the coating antibody, rabbit anti-human α1-AT IgG (Boehringer-Mannheim) was used as the capture antibody, and peroxidase-conjugated goat anti-rabbit Ig (Dako) was used as the detection antibody. The assay detected purified human α1-AT and α1-AT in human serum at concentrations as low as 0.1 ng/ml, but did not detect any α1-AT in serum from non-transgenic mice. The results are shown in FIG. 5. Of the seven mice in the study, three had baseline levels of human α1-AT of 300–400 μg/ml while the remaining four had baseline levels of 600–700 μg/ml. In all cases, administration of 4-PBA increased human α1-AT levels by approximately 200 μg/ml by three days (FIGS. 5B, 5C). Levels of human α1-AT remained elevated for the entire 5 days of treatment. The levels had returned to baseline when measured 7 days after the end of treatment and did not rise above baseline when the same mice were given water (vehicle) by gavage for 5 days either before of after treatment with 4-PBA. For the combined data (Fig 5A), the increases in blood levels of human α1-ATZ during PBA treatment on days 3 and 5 were significantly different from those on day 12 (p<0.001) as determined by Student's t test. In mice with low baseline human α1-AT levels, treatment with 4-PBA resulted in blood levels of human α1-AT that were approximately 20%–25% of levels present in PIMM3.03 mice and normal humans. Carlson et al., *J. Clin. Invest.* 83:1183–90, 1989. In mice with higher baseline levels, blood levels of human α1-AT reached approximately 45%–50% of blood levels seen in PIMM3.03 mice and normal humans.

Example 8

In many cases, failure of mutant proteins to escape from the ER is due to temperature-sensitive protein folding defects, such that culture of cells at temperatures below 37° C. results in increased secretion of the protein. To determine if butyric acid derivatives increase secretion by thermal stabilization of the α1-ATZ protein, CJZ12B cells were incubated for 12 hours as described in Example 2 at the normal growth temperature of 37° C. or at 27° C. Cells were then subjected to pulse-chase labeling, immunoprecipitation and SDS-PAGE/fluorography as described in Example 2. The results are shown in FIG. 6. The results showed that incubation at 27° C. did not increase secretion of α1-ATZ, but did decrease degradation. FIG. 6A. These results further show that α1-ATZ is not a temperature sensitive mutant and so the increase in secretion seen following treatment with a butyric acid derivative is not due to thermal stabilization of the α1-ATZ protein. In addition, these results show that inhibition of ER degradation is not necessarily associated with enhanced secretion of α1-ATZ.

The experiment was repeated except that the temperature was raised to 42° C. instead of lowered to 27° C. As shown in FIG. 6B, raising the temperature to 42° C. resulted in both an inhibition of degradation and an increase in secretion of α1-ATZ. Also noted was the appearance of an approximately 65 kD intracellular polypeptide at 42° C. The nature of this polypeptide is unknown. It has previously been reported that increasing the temperature of 37° C. to 42° C. results in increased polymerization of α1-ATZ in vitro. Lomas et al., Nature, 357:605–7, 1992. These results indicate that temperature has multiple and complex effects on the fate of α1-ATZ.

In light of the detailed description of the invention and the examples presented above, it can be appreciated that the several aspects of the invention are achieved.

It is to be understood that the present invention has been described in detail by way of illustration and example in order to acquaint others skilled in the art with the invention, its principles, and its practical application. Particular formulations and processes of the present invention are not limited to the descriptions of the specific embodiments presented, but rather the descriptions and examples should be viewed in terms of the claims that follow and their equivalents. While some of the examples and descriptions above include some conclusions about the way the invention may function, the inventor does not intend to be bound by those conclusions and functions, but puts them forth only as possible explanations.

It is to be further understood that the specific embodiments of the present invention as set forth are not intended as being exhaustive or limiting of the invention, and that many alternatives, modifications, and variations will be apparent to those skilled in the art in light of the foregoing examples and detailed description. Accordingly, this invention is intended to embrace all such alternatives, modifications, and variations that fall within the spirit and scope of the following claims.

What is claimed is:

1. A method for treating alpha-1-antitrypsin deficiency comprising administering to a vertebrate animal with alpha-1-antitrypsin deficiency an alpha-1-antitrypsin secretion stimulating amount of a compound of formula I:

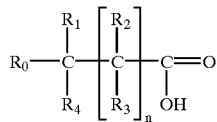

wherein
R₀ is an aryl, phenoxy, substituted aryl or substituted phenoxy wherein the substituents are selected from the group consisting of halogen, lower alkyl and hydroxy;
R₁, R₂, R₃, and R₄ are, independently, H, a lower alkoxy, a lower straight or branched chain alkyl, or a halogen; and
n is an integer from 0 to 2;
or a pharmaceutically acceptable salt or ester of a compound of formula I; or a mixture of compounds of formula I; or a mixture of pharmaceutically acceptable salts of formula I.

2. The method of claim 1, wherein the alpha-1-antitrypsin deficiency is due to a protease inhibitor type Z (PiZ) mutation.

3. The method of claim 1, wherein the compound is chosen from the group consisting of phenylbutyric acid, phenylproprionic acid, phenylacetic acid, phenylbutyrate, phenylproprionate, phenylacetate, phenoxybutyric acid, phenoxyproprionic acid, phenoxyacetic acid, phenoxybutyrate, phenoxyproprionate, phenoxyacetate, bromophenylbutyric acid, bromophenylproprionic acid, bromophenylacetic acid, bromophenylbutyrate, bromophenylproprionate, bromophenylacetate, chlorophenylbutyric acid, chlorophenylproprionic acid, chlorophenylacetic acid, chlorophenylbutyrate, chlorophenylproprionate, chlorophenylacetate, fluorophenylbutyric acid, fluorophenylproprionic acid, fluorophenylacetic acid, fluorophenylbutyrate, fluorophenylproprionate, fluorophenylacetate, iodophenylbutyric acid, iodophenylproprionic acid, iodophenylacetic acid, iodophenylbutyrate, iodophenylproprionate, iodophenylacetate, hydroxyphenylbutyric acid, hydroxyphenylproprionic acid, hydroxyphenylacetic acid, hydroxyphenylbutyrate, hydroxyphenylproprionate, hydroxyphenylacetate, methylphenylbutyric acid, methylphenylproprionic acid, methylphenylacetic acid, methylphenylbutyrate, methylphenylproprionate, methylphenylacetate, ethylphenylbutyric acid, ethylphenylproprionic acid, ethylphenylacetic acid, ethylphenylbutyrate, ethylphenylproprionate, ethylphenylacetate, naphthylbutyric acid, naphthylproprionic acid, naphthylacetic acid, naphthylbutyrate, naphthylproprionate, and naphthylacetate.

4. The method of claim 1, wherein the compound is chosen from the group consisting of phenylbutyric acid, phenylbutyrate, phenylacetic acid, and phenylacetate.

5. The method of claim 1, wherein the amount administered is between about 10 mg/kg body weight/day to about 1000 mg/kg body weight/day.

6. The method of claim 1, further comprising diagnosing alpha-1-antitrypsin deficiency.

7. The method of claim 1, further comprising monitoring alpha-1-antitrypsin levels.

8. A method for treating alpha-1-antitrypsin deficiency comprising administering to a vertebrate animal with alpha-1-antitrypsin deficiency caused by a protease inhibitor type Z (PiZ) mutation between about 10 mg/kg body weight/day to about 1000 mg/kg body weight/day of 4-phenylbutyrate.

9. A method for treating alpha-1-antitrypsin deficiency comprising, diagnosing alpha-1-antitrypsin deficiency due to the presence of a protease inhibitor type Z (PiZ) mutation;

administering between about 10 mg/kg of body weight/day to about 1000 mg/kg body weight/day of 4-phenylbutyrate; and monitoring levels of alpha-1-antitrypsin.

10. A method for treating liver disease caused by alpha-1-antitrypsin deficiency comprising administering to a vertebrate animal with alpha-1-antitrypsin deficiency an alpha-1-antitrypsin secretion stimulating amount of a compound of formula I:

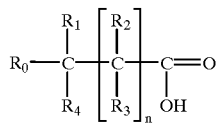

wherein $R_0$ is an aryl, phenoxy, substituted aryl or substituted phenoxy wherein the substituents are selected from the group consisting of halogen, lower alkyl and hydroxy;

$R_1$, $R_2$, $R_3$, and $R_4$ are, independently, H, a lower alkoxy, a lower straight or branched chain alkyl, or a halogen;

n is an integer from 0 to 2;

or a pharmaceutically acceptable salt or ester of a compound of formula I; or a mixture of compounds of formula I; or a mixture of pharmaceutically acceptable salts of formula I.

11. The method of claim 10, wherein the alpha-1-antitrypsin deficiency is due to a protease inhibitor type Z (PiZ) mutation.

12. The method of claim 10, wherein the compound is selected from the group consisting of phenylbutyric acid, phenylproprionic acid, phenylacetic acid, phenylbutyrate, phenylproprionate, phenylacetate, phenoxybutyric acid, phenoxyproprionic acid, phenoxyacetic acid, phenoxybutyrate, phenoxyproprionate, phenoxyacetate, bromophenylbutyric acid, bromophenylproprionic acid, bromophenylacetic acid, bromophenylbutyrate, bromophenylproprionate, bromophenylacetate, chlorophenylbutyric acid, chlorophenylproprionic acid, chlorophenylacetic acid, chlorophenylbutyrate, chlorophenylproprionate, chlorophenylacetate, fluorophenylbutyric acid, fluorophenylproprionic acid, fluorophenylacetic acid, fluorophenylbutyrate, fluorophenylproprionate, fluorophenylacetate, iodophenylbutyric acid, iodophenylproprionic acid, iodophenylacetic acid, iodophenylbutyrate, iodophenylproprionate, iodophenylacetate, hydroxyphenylbutyric acid, hydroxyphenylproprionic acid, hydroxyphenylacetic acid, hydroxyphenylbutyrate, hydroxyphenylproprionate, hydroxyphenylacetate, methylphenylbutyric acid, methylphenylproprionic acid, methylphenylacetic acid, methylphenylbutyrate, methylphenylproprionate, methylphenylacetate, ethylphenylbutyric acid, ethylphenylproprionic acid, ethylphenylacetic acid, ethylphenylbutyrate, ethylphenylproprionate, ethylphenylacetate, naphthylbutyric acid, naphthylproprionic acid, naphthylacetic acid, naphthylbutyrate, naphthylproprionate, and naphthylacetate.

13. The method of claim 10, wherein the compound is chosen from the group consisting of phenylbutyric acid, phenylbutyrate, phenylacetic acid, and phenylacetate.

14. The method of claim 10, wherein the amount administered is between about 10 mg/kg body weight/day to about 1000 mg/kg body weight/day.

15. The method of claim 10, further comprising diagnosing alpha-1-antitrypsin deficiency.

16. The method of claim 10, further comprising monitoring alpha-1-antitrypsin levels.

17. A method for treating liver disease caused by alpha-1-antitrypsin deficiency comprising administering to a vertebrate animal with alpha-1-antitrypsin deficiency caused by a protease inhibitor type Z (PiZ) mutation between about 10 mg/kg body weight/day to about 1000 mg/kg body weight/day of 4-phenylbutyrate.

18. A method for treating liver disease caused by alpha-1-antitrypsin deficiency comprising, diagnosing alpha-1-antitrypsin deficiency due to the presence of a protease inhibitor type Z (PiZ) mutation;

administering between about 10 mg/kg of body weight/day to about 1000 mg/kg body weight/day of 4-phenylbutyrate; and monitoring levels of alpha-1-antitrypsin.

19. A method for preventing or inhibiting liver disease caused by alpha-1-antitrypsin deficiency comprising administering to a vertebrate animal with alpha-1-antitrypsin deficiency an alpha-1-antitrypsin secretion stimulating amount of a compound of formula I:

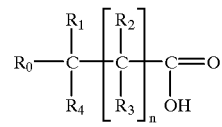

wherein $R_0$ is an aryl, phenoxy, substituted aryl or substituted phenoxy wherein the substituents are selected from the group consisting of halogen, lower alkyl and hydroxy;

$R_1$, $R_2$, $R_3$, and $R_4$ are, independently, H, a lower alkoxy, a lower straight or branched chain alkyl, or a halogen;

n is an integer from 0 to 2;

or a pharmaceutically acceptable salt or ester of a compound of formula I; or a mixture of compounds of formula I; or a mixture of pharmaceutically acceptable salts of formula I.

20. The method of claim 19, wherein the alpha-1-antitrypsin deficiency is due to a protease inhibitor type Z (PiZ) mutation.

21. The method of claim 19, wherein the compound is selected from the group consisting of phenylbutyric acid, phenylproprionic acid, phenylacetic acid, phenylbutyrate, phenylproprionate, phenylacetate, phenoxybutyric acid, phenoxyproprionic acid, phenoxyacetic acid, phenoxybutyrate, phenoxyproprionate, phenoxyacetate, bromophenylbutyric acid, bromophenylproprionic acid, bromophenylacetic acid, bromophenylbutyrate, bromophenylproprionate, bromophenylacetate, chlorophenylbutyric acid, chlorophenylproprionic acid, chlorophenylacetic acid, chlorophenylbutyrate, chlorophenylproprionate, chlorophenylacetate, fluorophenylbutyric acid, fluorophenylproprionic acid, fluorophenylacetic acid, fluorophenylbutyrate, fluorophenylproprionate, fluorophenylacetate, iodophenylbutyric acid, iodophenylproprionic acid, iodophenylacetic acid, iodophenylbutyrate, iodophenylproprionate, iodophenylacetate, hydroxyphenylbutyric acid, hydroxyphenylproprionic acid, hydroxyphenylacetic acid, hydroxyphenylbutyrate, hydroxyphenylproprionate, hydroxyphenylacetate, methylphenylbutyric acid, methylphenylproprionic acid, methylphenylacetic acid, methylphenylbutyrate, methylphenylproprionate, methylphenylacetate, ethylphenylbutyric acid, ethylphenylproprionic acid, ethylphenylacetic acid, ethylphenylbutyrate, ethylphenylproprionate, ethylphenylacetate, naphthylbutyric acid, naphthylproprionic acid, naphthylacetic acid, naphthylbutyrate, naphthylproprionate, and naphthylacetate.

22. The method of claim 19, wherein the compound is chosen from the group consisting of phenylbutyric acid, phenylbutyrate, phenylacetic acid, and phenylacetate.

23. The method of claim 19, wherein the amount administered is between about 10 mg/kg body weight/day to about 1000 mg/kg body weight/day.

24. The method of claim 19, further comprising diagnosing alpha-1-antitrypsin deficiency.

25. The method of claim 19, further comprising monitoring alpha-1-antitrypsin levels.

26. A method for preventing or inhibiting liver disease caused by alpha-1-antitrypsin deficiency comprising administering to a vertebrate animal with alpha-1-antitrypsin deficiency caused by a protease inhibitor type Z (PiZ) mutation between about 10 mg/kg body weight/day and about 1000 mg/kg body weight/day of 4-phenylbutyrate.

27. A method for preventing or inhibiting liver disease caused by alpha-1-antitrypsin deficiency comprising,
  diagnosing alpha-1-antitrypsin deficiency due to the presence of a protease inhibitor type Z (PiZ) mutation;
  administering between about 10 mg/kg of body weight/day to about 1000 mg/kg body weight/day of 4-phenylbutyrate; and
  monitoring levels of alpha-1-antitrypsin.

28. A method for treating emphysema in animals with alpha-1-antitrypsin deficiency comprising administering to a vertebrate animal with alpha-1-antitrypsin deficiency an alpha-1-antitrypsin secretion stimulating amount of a compound of formula I:

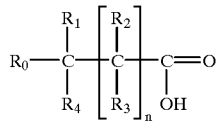

wherein
  $R_0$ is an aryl, phenoxy, substituted aryl or substituted phenoxy wherein the substituents are selected from the group consisting of halogen, lower alkyl and hydroxy;
  $R_1$, $R_2$, $R_3$, and $R_4$ are, independently, H, a lower alkoxy, a lower straight or branched chain alkyl, or a halogen;
  n is an integer from 0 to 2;
  or a pharmaceutically acceptable salt or ester of a compound of formula I; or a mixture of compounds of formula I; or a mixture of pharmaceutically acceptable salts of formula I.

29. The method of claim 28, wherein the alpha-1-antitrypsin deficiency is due to a protease inhibitor type Z (PiZ) mutation.

30. The method of claim 28, wherein the compound is selected from the group consisting of phenylbutyric acid, phenylproprionic acid, phenylacetic acid, phenylbutyrate, phenylproprionate, phenylacetate, phenoxybutyric acid, phenoxyproprionic acid, phenoxyacetic acid, phenoxybutyrate, phenoxyproprionate, phenoxyacetate, bromophenylbutyric acid, bromophenylproprionic acid, bromophenylacetic acid, bromophenylbutyrate, bromophenylproprionate, bromophenylacetate, chlorophenylbutyric acid, chlorophenylproprionic acid, chlorophenylacetic acid, chlorophenylbutyrate, chlorophenylproprionate, chlorophenylacetate, fluorophenylbutyric acid, fluorophenylproprionic acid, fluorophenylacetic acid, fluorophenylbutyrate, fluorophenylproprionate, fluorophenylacetate, iodophenylbutyric acid, iodophenylproprionic acid, iodophenylacetic acid, iodophenylbutyrate, iodophenylproprionate, iodophenylacetate, hydroxyphenylbutyric acid, hydroxyphenylproprionic acid, hydroxyphenylacetic acid, hydroxyphenylbutyrate, hydroxyphenylproprionate, hydroxyphenylacetate, methylphenylbutyric acid, methylphenylproprionic acid, methylphenylacetic acid, methylphenylbutyrate, methylphenylproprionate, methylphenylacetate, ethylphenylbutyric acid, ethylphenylproprionic acid, ethylphenylacetic acid, ethylphenylbutyrate, ethylphenylproprionate, ethylphenylacetate, naphthylbutyric acid, naphthylproprionic acid, naphthylacetic acid, naphthylbutyrate, naphthylproprionate, and naphthylacetate.

31. The method of claim 28, wherein the compound is chosen from the group consisting of phenylbutyric acid, phenylbutyrate, phenylacetic acid and phenylacetate.

32. The method of claim 28, wherein the amount administered is between about 10 mg/kg body weight/day to about 1000 mg/kg body weight/day.

33. The method of claim 28, further comprising diagnosing alpha-1-antitrypsin deficiency.

34. The method of claim 28, further comprising monitoring alpha-1-antitrypsin levels.

35. A method for treating emphysema in animals with alpha-1-antitrypsin deficiency comprising administering to a vertebrate animal with alpha-1-antitrypsin deficiency caused by a protease inhibitor type Z (PiZ) mutation between about 10 mg/kg body weight/day to about 1000 mg/kg body weight/day of 4-phenylbutyrate.

36. A method for treating emphysema caused by alpha-1-antitrypsin deficiency comprising,
  diagnosing alpha-1-antitrypsin deficiency due to the presence of a protease inhibitor type Z (PiZ) mutation;
  administering between about 10 mg/kg of body weight/day to about 1000 mg/kg body weight/day of 4-phenylbutyrate; and
  monitoring levels of alpha-1-antitrypsin.

37. A method for preventing or inhibiting emphysema in animals with alpha-1-antitrypsin deficiency comprising administering to a vertebrate animal with alpha-1-antitrypsin deficiency an alpha-1-antitrypsin secretion stimulating amount of a compound of formula I:

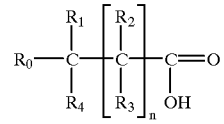

wherein
  $R_0$ is an aryl, phenoxy, substituted aryl or substituted phenoxy wherein the substituents are selected from the group consisting of halogen, lower alkyl and hydroxy;
  $R_1$, $R_2$, $R_3$, and $R_4$ are, independently, H, a lower alkoxy, a lower straight or branched chain alkyl, or a halogen;
  n is an integer from 0 to 2;
  or a pharmaceutically acceptable salt or ester of a compound of formula I; or a mixture of compounds of formula I; or a mixture of pharmaceutically acceptable salts of formula I.

38. The method of claim 37, wherein the alpha-1-antitrypsin deficiency is due to a protease inhibitor type Z (PiZ) mutation.

39. The method of claim 37, wherein the compound is selected from the group consisting of phenylbutyric acid, phenylproprionic acid, phenylacetic acid, phenylbutyrate, phenylproprionate, phenylacetate, phenoxybutyric acid, phenoxyproprionic acid, phenoxyacetic acid, phenoxybutyrate, phenoxyproprionate, phenoxyacetate, bromophenylbutyric acid, bromophenylproprionic acid, bromophenylacetic acid, bromophenylbutyrate, bromophenylproprionate, bromophenylacetate, chlorophenylbutyric acid, chlorophenylproprionic acid, chlorophenylacetic acid, chlorophenylbutyrate, chlorophenylproprionate, chlorophenylacetate, fluorophenylbutyric acid, fluorophenylproprionic acid, fluorophenylacetic acid, fluorophenylbutyrate, fluorophenylproprionate, fluorophenylacetate, iodophenylbutyric acid, iodophenylproprionic acid, iodophenylacetic acid, iodophenylbutyrate, iodophenylproprionate, iodophenylacetate, hydroxyphenylbutyric acid, hydroxyphenylproprionic acid, hydroxyphenylacetic acid, hydroxyphenylbutyrate, hydroxyphenylproprionate, hydroxyphenylacetate, methylphenylbutyric acid, methylphenylproprionic acid, methylphenylacetic acid, methylphenylbutyrate, methylphenylproprionate, methylphenylacetate, ethylphenylbutyric acid, ethylphenylproprionic acid, ethylphenylacetic acid, ethylphenylbutyrate, ethylphenylproprionate, ethylphenylacetate, naphthylbutyric acid, naphthylproprionic acid, naphthylacetic acid, naphthylbutyrate, naphthylproprionate, and naphthylacetate.

40. The method of claim 37, wherein the compound is chosen from the group consisting of phenylbutyric acid, phenylbutyrate, phenylacetic acid and phenylacetate.

41. The method of claim 37, wherein the amount administered is between about 10 mg/kg body weight/day to about 1000 mg/kg body weight/day.

42. The method of claim 37, further comprising diagnosing alpha-1-antitrypsin deficiency.

43. The method of claim 37, further comprising monitoring alpha-1-antitrypsin levels.

44. A method for preventing or inhibiting of emphysema in animals with alpha-1-antitrypsin deficiency comprising administering to a vertebrate animal with alpha-1-antitrypsin deficiency caused by a protease inhibitor type Z (PiZ) mutation between about 10 mg/kg body weight/day to about 1000 mg/kg body weight/day of 4-phenylbutyrate.

45. A method for preventing or inhibiting emphysema caused by alpha-1-antitrypsin deficiency comprising, diagnosing alpha-1-antitrypsin deficiency due to the presence of a protease inhibitor type Z (PiZ) mutation;

administering between about 10 mg/kg of body weight/day to about 1000 mg/kg body weight/day of 4-phenylbutyrate; and monitoring levels of alpha-1-antitrypsin.

46. A method for increasing the secretion of alpha-1-antitrypsin by a cell comprising, contacting a cell containing a protease inhibitor type Z (PiZ) mutation with a an alpha-1-antitrypsin secretion stimulating amount of a compound of formula I:

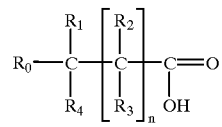

wherein $R_0$ is an aryl, phenoxy, substituted aryl or substituted phenoxy wherein the substituents are selected from the group consisting of halogen, lower alkyl and hydroxy;

$R_1$, $R_2$, $R_3$, $R_4$ are, independently, H, a lower alkoxy, a lower straight or branched chain alkyl, or a halogen;

n is an integer from 0 to 2;

or a salt or ester of a compound of formula I; or a mixture of compounds of formula I; or a mixture of salts of formula I.

47. The method of claim 31, wherein the compound is selected from the group consisting of phenylbutyric acid, phenylproprionic acid, phenylacetic acid, phenylbutyrate, phenylproprionate, phenylacetate, phenoxybutyric acid, phenoxyproprionic acid, phenoxyacetic acid, phenoxybutyrate, phenoxyproprionate, phenoxyacetate, bromophenylbutyric acid, bromophenylproprionic acid, bromophenylacetic acid, bromophenylbutyrate, bromophenylproprionate, bromophenylacetate, chlorophenylbutyric acid, chlorophenylproprionic acid, chlorophenylacetic acid, chlorophenylbutyrate, chlorophenylproprionate, chlorophenylacetate, fluorophenylbutyric acid, fluorophenylproprionic acid, fluorophenylacetic acid, fluorophenylbutyrate, fluorophenylproprionate, fluorophenylacetate, iodophenylbutyric acid, iodophenylproprionic acid, iodophenylacetic acid, iodophenylbutyrate, iodophenylproprionate, iodophenylacetate, hydroxyphenylbutyric acid, hydroxyphenylproprionic acid, hydroxyphenylacetic acid, hydroxyphenylbutyrate, hydroxyphenylproprionate, hydroxyphenylacetate, methylphenylbutyric acid, methylphenylproprionic acid, methylphenylacetic acid, methylphenylbutyrate, methylphenylproprionate, methylphenylacetate, ethylphenylbutyric acid, ethylphenylproprionic acid, ethylphenylacetic acid, ethylphenylbutyrate, ethylphenylproprionate, ethylphenylacetate, naphthylbutyric acid, naphthylproprionic acid, naphthylacetic acid, naphthylbutyrate, naphthylproprionate, and naphthylacetate.

48. The method of claim 47, wherein the compound is chosen from the group consisting of phenylbutyric acid, phenylbutyrate, phenylacetic acid and phenylacetate.

49. The method of claim 47, wherein the amount of the alpha-1-antitrypsin secretion stimulating compound is between about 0.1 mM and about 100 mM.

* * * * *

UNITED STATES PATENT AND TRADEMARK OFFICE
CERTIFICATE OF CORRECTION

PATENT NO.      : 6,403,646 B1
DATED           : June 11, 2002
INVENTOR(S)     : David H. Perlmutter et al.

It is certified that error appears in the above-identified patent and that said Letters Patent is hereby corrected as shown below:

Column 22,
Line 12, "$R_3$, $R_4$" should read -- $R_3$, and $R_4$ --.

Signed and Sealed this

Eighteenth Day of February, 2003

JAMES E. ROGAN
*Director of the United States Patent and Trademark Office*